United States Patent [19]
Keith et al.

[11] Patent Number: 5,667,490
[45] Date of Patent: Sep. 16, 1997

[54] ABLATION DEVICE DRIVE ASSEMBLY INCLUDING CATHETER CONNECTOR

[75] Inventors: Peter T. Keith, Fridley; Robert E. Atkinson, St. Anthony; Thomas V. Ressemann; Hans Mische, both of St. Cloud, all of Minn.

[73] Assignee: SciMed Life Systems, Inc., Maple Grove, Minn.

[21] Appl. No.: 415,759

[22] Filed: Apr. 3, 1995

Related U.S. Application Data

[63] Continuation of Ser. No. 212,319, Mar. 14, 1994, abandoned, which is a continuation of Ser. No. 960,531, Oct. 7, 1992, abandoned.

[51] Int. Cl.$^6$ .................................................... A61B 17/20
[52] U.S. Cl. .......................... 604/22; 604/283; 604/905; 206/159; 206/171; 173/220
[58] Field of Search ................... 606/159, 166–171; 604/22, 42, 283, 280, 905, 903; 483/98; 173/220, 165, 167; 74/12

[56] References Cited

U.S. PATENT DOCUMENTS

| | | |
|---|---|---|
| 4,445,509 | 5/1984 | Auth . |
| 4,591,355 | 5/1986 | Hilse ........................... 604/159 |
| 4,646,736 | 3/1987 | Auth . |
| 4,679,557 | 7/1987 | Opie et al. . |
| 4,728,319 | 3/1988 | Masch ............................... 604/22 |
| 4,747,406 | 5/1988 | Nash . |
| 4,771,774 | 9/1988 | Simpson et al. ................... 604/180 |
| 4,792,327 | 12/1988 | Swartz .............................. 606/170 |
| 4,917,085 | 4/1990 | Smith ............................... 606/159 |
| 4,957,482 | 9/1990 | Shiber .............................. 604/22 |
| 4,969,879 | 11/1990 | Lichte .............................. 604/283 |
| 4,990,134 | 2/1991 | Auth ................................ 604/22 |
| 5,002,553 | 3/1991 | Shiber .............................. 606/159 |
| 5,019,089 | 5/1991 | Farr . |
| 5,030,201 | 7/1991 | Palestrant . |
| 5,135,483 | 8/1992 | Wagner et al. .................... 604/22 |
| 5,171,214 | 12/1992 | Kober et al. ...................... 604/82 |
| 5,217,474 | 6/1993 | Zacca et al. ...................... 606/170 |
| 5,308,354 | 5/1994 | Zacca et al. ...................... 606/170 |
| 5,314,407 | 5/1994 | Auth et al. ....................... 604/222 |
| 5,393,101 | 2/1995 | Matkovich ......................... 285/3 |
| 5,417,672 | 5/1995 | Nita et al. ........................ 604/285 |

FOREIGN PATENT DOCUMENTS

| | | |
|---|---|---|
| 0 117519 A1 | 9/1984 | European Pat. Off. . |
| 3519626 A1 | 12/1986 | Germany . |
| 2 044 103A | 10/1980 | United Kingdom . |

*Primary Examiner*—Mark O. Polutta
*Attorney, Agent, or Firm*—Nawrocki, Rooney & Sivertson

[57] ABSTRACT

A drive assembly for an ablation device. The drive assembly including a housing and a connector for coupling a catheter assembly including a rotatable drive shaft to the housing. The connector including a first coupling rotatably connected to the housing and a second coupling fixably connected to the housing.

6 Claims, 4 Drawing Sheets

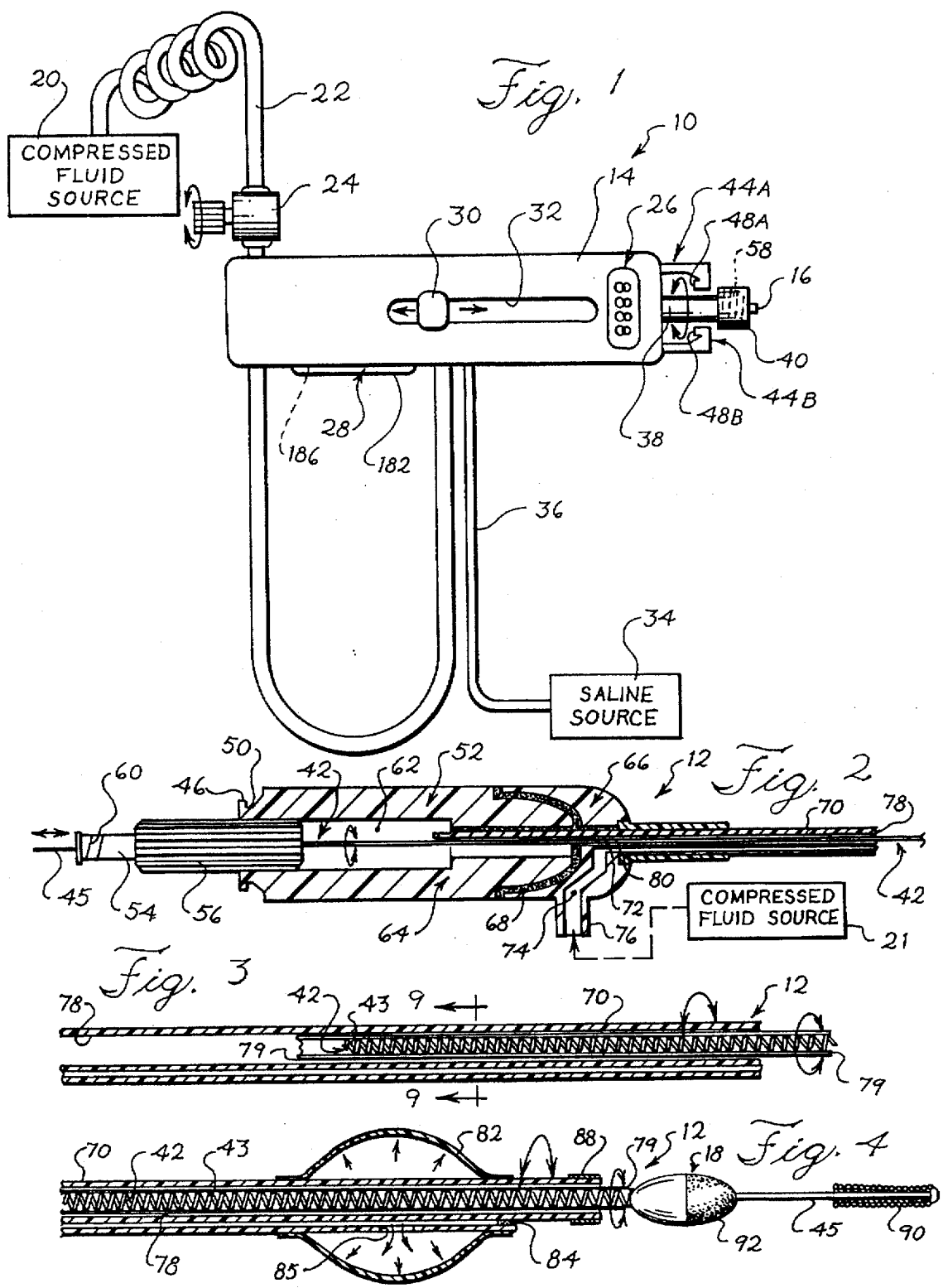

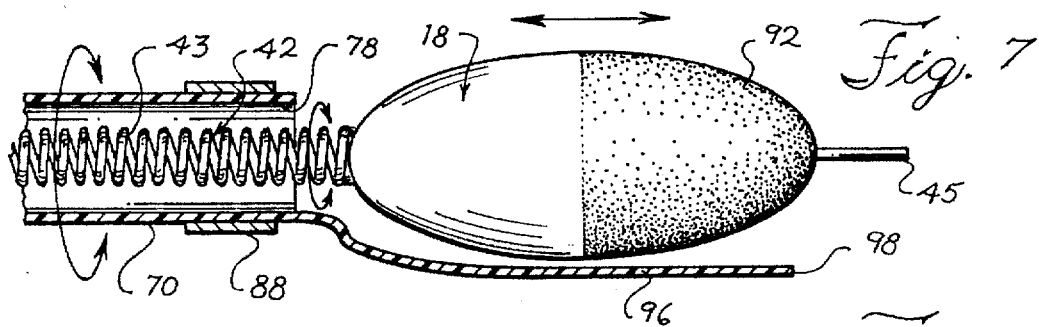
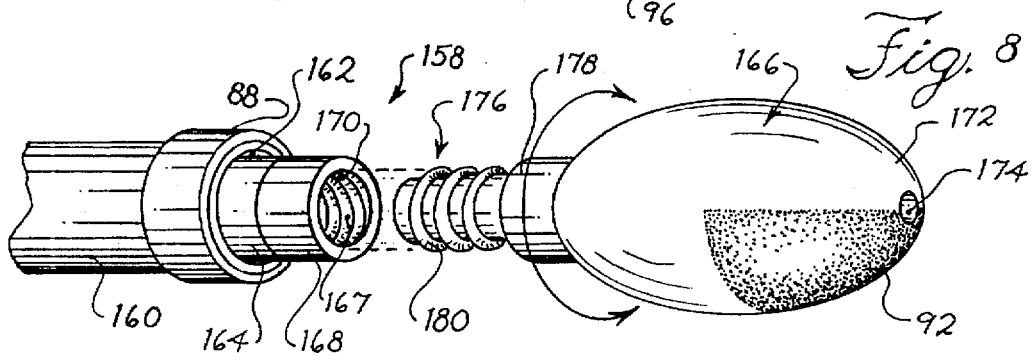
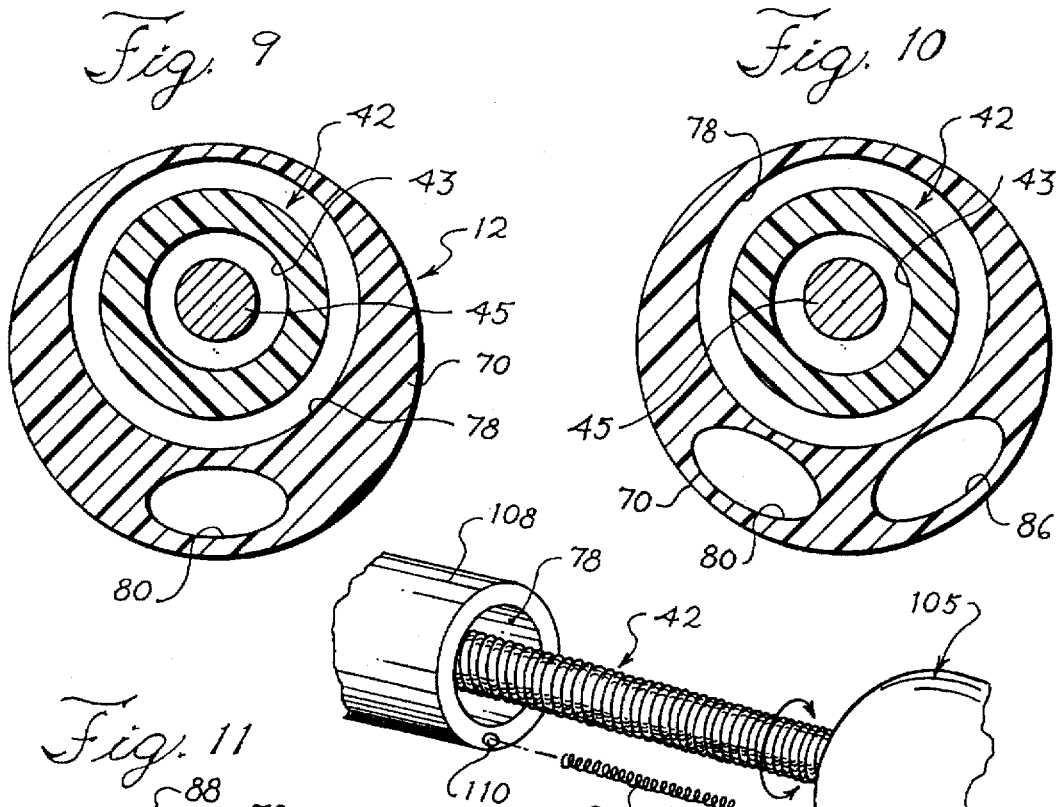
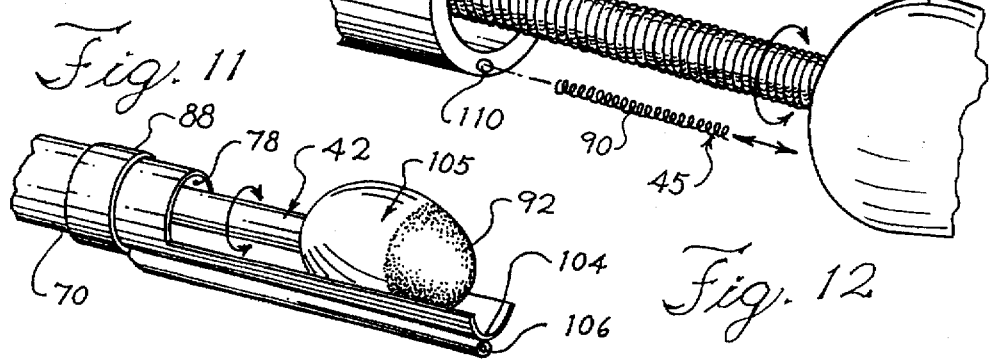

ABLATION DEVICE DRIVE ASSEMBLY INCLUDING CATHETER CONNECTOR

This application is a continuation of U.S. application Ser. No. 08/212,319 filed Mar. 14, 1994 now abandoned which is a continuation of U.S. application Ser. No. 07/960,531 filed Oct. 7, 1992 now abandoned.

BACKGROUND OF THE INVENTION

The present invention generally relates to intravascular devices for ablating obstructive material from a patient's vasculature, and more specifically, to novel improvements in a particular type of occlusion ablation devices and improved methods of using those devices.

Several types of intravascular devices are known for ablating occlusions from vascular lumens. The following United States patents disclose teachings relating to a type of such devices that is intended to ablate vascular occlusion material.

| Auth | 4,445,509 | May 1, 1984 |
| Auth | 4,646,739 | March 3, 1987 |
| Auth | 4,990,134 | February 5, 1991 |

While these ablation devices function well, there is always room for improvement. Notably, there are a number of aspects of the ablation devices as disclosed in the Auth patents, among other occlusion material ablation devices, which are ripe for improvement. Improvements of the prior art ablation devices which address these aspects may increase their performance, thereby possibly rendering them more attractive to certain physicians, clinicians, and other medical professionals for given applications.

Specifically, these prior an devices may comprise fixedly joined, unitary drive and catheter assemblies. Because these two assemblies are not separable, and because the portion of these assemblies that remains outside of the patient's body is often bulky, the associated catheter assembly may be cumbersome and sometimes difficult to manipulate. The bulky nature of these devices may increase the difficulty of catheter insertion into a patient, tracking the catheter along a medical guidewire in a patient's vascular lumen, and placement of a distal end of the catheter in appropriate proximity to a stenosis or occlusion within the vasculature.

Permanent attachment of the drive assembly and the catheter assembly may decrease a physician's tactile feel of the movement of the catheter within a vascular lumen and along a medical guidewire. The decreased tactile feel may make it relatively difficult for a medical professional to properly and efficiently place the catheter assembly within the vascular lumen. The reduced tactile feel and increased handling difficulty may make the functionality of these prior art vascular occlusion ablation devices suboptimal. Furthermore, some of these ablation devices may have limited compatibility with currently existing percutaneous transluminal coronary angioplasty (hereinafter "PTCA") equipment, thereby limiting use of those devices.

During the course of an occlusion ablation procedure, it may be desirable or necessary to change an abrading or ablating burr to properly ablate the stenosis, e.g. to change effective ablating diameter. Because the drive assembly and the catheter assembly are fixedly connected, the entire catheter assembly must be removed from the patient and replaced by another catheter to change the dimensions or ablating characteristics of the ablating burr. These devices are not reusable and are intended to be disposable, which means that each time an ablating burr is changed, an entirely new device must be employed, thereby possibly significantly increasing the cost of the procedure. In addition, because an ablating burr on a given prior art device is not readily changeable, use of a particular one of these devices may extend the procedure time.

The construction of the prior art ablation devices allows those devices to ablate along the entirety of a three hundred and sixty degree arc within a vascular lumen as the ablating burr is rotated by a drive shaft. While this degree of ablation may be desirable in some situations, it may be undesirable in others. Notably, stenosis deposits may have an eccentric configuration and may not reside along an entire three hundred and sixty degree portion of an interior surface of a lumen. If the prior art ablating burrs are used, thereby ablating along a three hundred and sixty degree arc along the interior surface of the lumen, some healthy vascular tissue may be ablated along with the occlusive material.

During any intravascular procedure, it is a concern that particulate debris formed may become embolized. Some of the prior art ablation devices do not utilize a method of aspiration or other means for removing the debris from the patient's vascular system. It is believed that the presence of sufficiently small particulate will not harm the patient. In theory, the particulate thusly formed is so small as to not form an embolism intravascularly and, therefore, to float freely through a patient's vascular system without adverse effects. However, there is always room for improvement in the prior art, and it may be desirable in certain circumstances, such as when a large amount of stenosis or lesion is disposed along the vascular lumen interior surface or when the lesion is heavily calcified, to provide some means or method for positively removing the particulate from the patient's vasculature.

Some prior art ablation devices do provide some sort of means for removing particulate debris generated by operation of the device. However, some constructions of these means can be improved. Specifically, these prior art debris removal means generally comprise a lumen in the catheter assembly for applying a vacuum or negative pressure at the distal end of the catheter assembly. This lumen is often shared by the drive shaft which conjointly rotates the ablating burr. When vacuum is applied to the catheter drive shaft lumen, the debris drawn into the lumen can engage the drive shaft. If sufficient debris engages the drive shaft, the rotation of the shaft, and thus the rotation of the ablating burr, may be limited.

As a vascular occlusion material ablation procedure is performed, the catheter assembly is progressively axially moved along a guidewire, which often passes through an appropriate lumen in the catheter assembly. Some of the prior art devices have lumens of a configuration which limits the types of guidewires that can be used therewith. This is not desirable as it may limit selection of guidewire types available to the physician. In addition, the configuration of the catheter guidewire lumen may limit the tractability of the catheter over the guidewire, thereby increasing the difficulty of catheter placement and navigation, within a vascular lumen.

In some instances, the tractability may be so limited that the physician has to rotate the guidewire and/or the catheter assembly in order to overcome navigation-inhibiting friction or torque generated between the guidewire and the catheter assembly and/or between the ablating burr or catheter assembly and a stenosis or lesion. The friction causing the limited tractability of the catheter assembly may also cause the guidewire or the drive shaft to contort or bend. These contortions can give rise to spring-like forces within the guidewire and the drive shaft. When the friction or torque causing the contortions of the guidewire and/or the drive shaft cease or decrease sufficiently, the guidewire and/or the drive shaft can "leap forward" within the lumen (i.e. similar to the expansion of a compressed spring). This leaping forward may be increased when the ablating burr progresses through a stenosis because a higher magnitude spring-like force may be generated. These spring-like forces may also create a high torsional strain on the drive shaft, which may inhibit proper operation of the ablating burr.

As the prior art catheter assembly is moved through a patient's vascular system, the progress thereof can be monitored by radiography or other suitable imaging technique. In order to facilitate navigation in the vascular system lumens, a distal end of the guidewire is often provided with a radiopaque member, usually in the form of a coil or spring, thereby rendering that member visible intravascularly to the relevant medical professionals. Once the professional properly positions the guidewire with respect to the stenosis, the catheter assembly is advanced along the guidewire towards the distal end thereof and the stenosis. However, the distal end of the catheter assembly is often not radiopaque. Because the distal end of the catheter assembly is not intravascularly visible to the professional, he must infer the intravascular position of the catheter by "feeling" his way along the guidewire. Because the tactile feel of the catheter assembly may be reduced, as discussed above, precise placement of the distal end of the catheter assembly with respect to the stenosis may be relatively difficult as compared to placement of commonly used balloon catheters providing the physician with increased tactile feel.

Some of the prior art ablation devices do not allow for retraction of the guidewire behind or proximal of the ablating burr. Thus, in order for the ablating burr to engage the stenosis to be ablated, the guidewire must be located across the stenosis first. This may be relatively easy in cases where the stenosis extends only from a relatively small angular portion of the interior surface of the lumen and does not amount to a total occlusion of the lumen. However, if the stenosis creates a total occlusion of the lumen, the guidewire may have to be "punched through" the stenosis to allow the ablating burr to engage the stenosis for ablation or abrasion. Also, similar difficulties may be encountered when the vascular dimensions are insufficient to allow an ablating burr to effectively contact a stenosis, such as that encountered when a portion of a guidewire located distally of the ablating burr has dimensions greater than the available vascular dimensions.

When the physician positions the catheter assembly properly with respect to the stenosis, the physician can activate the drive assembly, thereby rotating the drive shaft and the ablating burr in order to ablate the stenosis. In order to adequately ablate vascular occlusion material, the rotational speed of the ablating burr should be closely monitored and controlled. The prior art ablation devices, however, do not provide means for easily monitoring the speed of the ablating burr. Furthermore, in some of the prior art devices, ablating burr speed is controlled by a foot pedal actuating a suitable speed regulator. This demands the physician to coordinate hand, eye, and foot movements in order to perform the relevant procedure.

Some of the ablation devices of the prior art, for example, ablate the stenosis by means of rotational movement of the ablating burr. While this ablating action may be acceptable in some cases, it is not in others, especially since a stenosis often has an eccentric configuration within a vascular lumen.

Rotation of the ablating burr can lead to ablating along a three hundred and sixty degree arc along a vascular lumen interior surface. Also, rotation of the ablating burr may prevent desired variance of the frequency and amplitude of ablating burr motion, which may be necessary or desirable to ablate a certain stenosis. Also, by simply rotating the ablating burr, the burr may not have sufficient differential cutting to distinguish between healthy tissues and diseased tissues of similar hardness.

In some instances, a physician may determine that, after vascular occlusion material ablation, or other means of intravascular treatment, balloon angioplasty may be required or desirable. This means that, with the prior art ablation devices, the device must be fully removed from the patient's vascular system and replaced by a balloon catheter. The balloon catheter may be able to utilize the same guidewire as the ablation device. But, as noted above, many of the prior ablation devices have limited compatibility with other, especially PTCA, equipment. Furthermore, the physician may have to insert and locate a new guidewire before he can insert the balloon catheter. These things can further complicate the procedure and also make it more expensive because multiple pieces of equipment are used.

The present invention provides a novel vascular occlusion material ablation device. The novel ablation device of the invention offers a number of improvements over the prior art ablation devices discussed hereinabove, for example, and represents a significant advancement in the field of intravascular treatments. This novel device and the improvements to ablation devices are intended to address some, if not all of the above-discussed concerns presented by the prior art ablation devices. The invention also provides novel, improved methods for vascular occlusion material ablation.

SUMMARY OF THE INVENTION

A general object of the present invention is to provide novel improvements in vascular occlusion material ablation devices.

A more specific object of the invention is to provide novel improvements in the ablation devices disclosed in the above-referenced patents to Auth.

Another object of the present invention is to provide a novel ablation device which is less bulky and easier to handle than some prior art ablation devices.

An additional object of the invention is to provide a novel ablation device comprising releasably joinable drive and catheter assemblies.

A further object of the present invention is to provide a novel ablation device which gives a medical professional increased tactile feel on an associated catheter as compared with some of the currently available ablation devices.

Another object of the invention is to provide an ablation device which facilitates relatively quick, easy and inexpensive ablating burr changes as compared to some of the prior art devices.

An additional object of the present invention is to provide a novel ablation device which can ablate selective portions of a stenosis.

A further object of the invention is to provide an ablation device having greater compatibility with currently available PTCA equipment than the prior art ablation devices of the above-referenced Auth patents.

Another object of the present invention is to provide a novel ablation device which can remove debris, formed by ablating a stenosis, from a vascular system, while insuring that the debris does not interfere with an associated drive shaft.

An additional object of the invention is to provide an ablation device which reduces interference of debris with operation of the device.

A further object of the present invention is to provide a novel ablation device which can dilate a lumen.

Another object of the invention is to provide a novel ablation device, a distal end of which is radiopaque.

An additional object of the present invention is to provide a novel ablation device including a drive assembly having means for allowing a physician to relatively easily monitor and control ablating burr speed.

A further object of the invention is to provide an ablation device having increased tractability over a guidewire, as compared to some prior art ablation devices.

A novel ablation device, constructed according to the teachings of the present invention, includes releasably joinable, drive and catheter assemblies. The drive assembly includes a tachometer assembly and a regulator for monitoring and controlling ablating burr speed. A dilating member is provided in addition to an ablating burr on the catheter assembly. The catheter tube may have multiple independent lumens having axes of elongation offset parallelly in the tube. Additionally, the ablating burr may be connected to the catheter tube by drive gears or releasable threads. A radiopaque member is included on the distal end of the catheter tube, thereby rendering it intravascularly visible to an observer. Novel, improved methods of ablating vascular deposits are also provided.

BRIEF DESCRIPTION OF THE DRAWINGS

The organization and manner of the structure and operation of the invention, together with further objects and advantages thereof, may best be understood by reference to the following description taken in connection with the accompanying drawings, wherein like reference numerals identify like elements in which:

FIG. 1 is a plan view of an improved novel drive assembly, constructed according to the teachings of the present invention, releasably joinable with a separate catheter assembly;

FIG. 2 is a partially sectioned side elevational view of a manifold assembly comprising a proximal portion of a novel catheter assembly releasably joinable to the drive assembly of FIG. 1;

FIG. 3 is an enlarged sectioned side elevational view of a portion of a catheter tube of the invention located distally of a manifold assembly;

FIG. 4 is an enlarged partially sectioned side elevational view of a distal portion of a catheter assembly, illustrating the novel construction thereof;

FIG. 7 is an enlarged, partially sectioned side elevational view of a distal portion of a catheter assembly, constructed according to the teachings of the present invention, having an ablating shield thereby allowing the assembly to selectively ablate a predetermined portion of a vascular lumen;

FIG. 8 is a fragmentary enlarged elevational view of another embodiment of a distal end of a catheter tube having a threadibly releasably attached ablation burr;

FIG. 9 is a sectional view, taken along line 9—9 of FIG. 3, illustrating the novel luminal construction of a catheter tube;

FIG. 10 is a view, similar to that of FIG. 9, showing an alternative embodiment of the novel catheter tube having multiple lumens;

FIG. 11 is a perspective view of an alternative construction of a distal end of the catheter assembly of the invention;

FIG. 12 is an enlarged perspective view of yet another alternative embodiment of the distal end of the novel catheter assembly, showing a guidewire retracted proximally of an ablating burr, thereby facilitating operation of the burr;

DETAILED DESCRIPTION OF PREFERRED EMBODIMENTS

Figure 5:
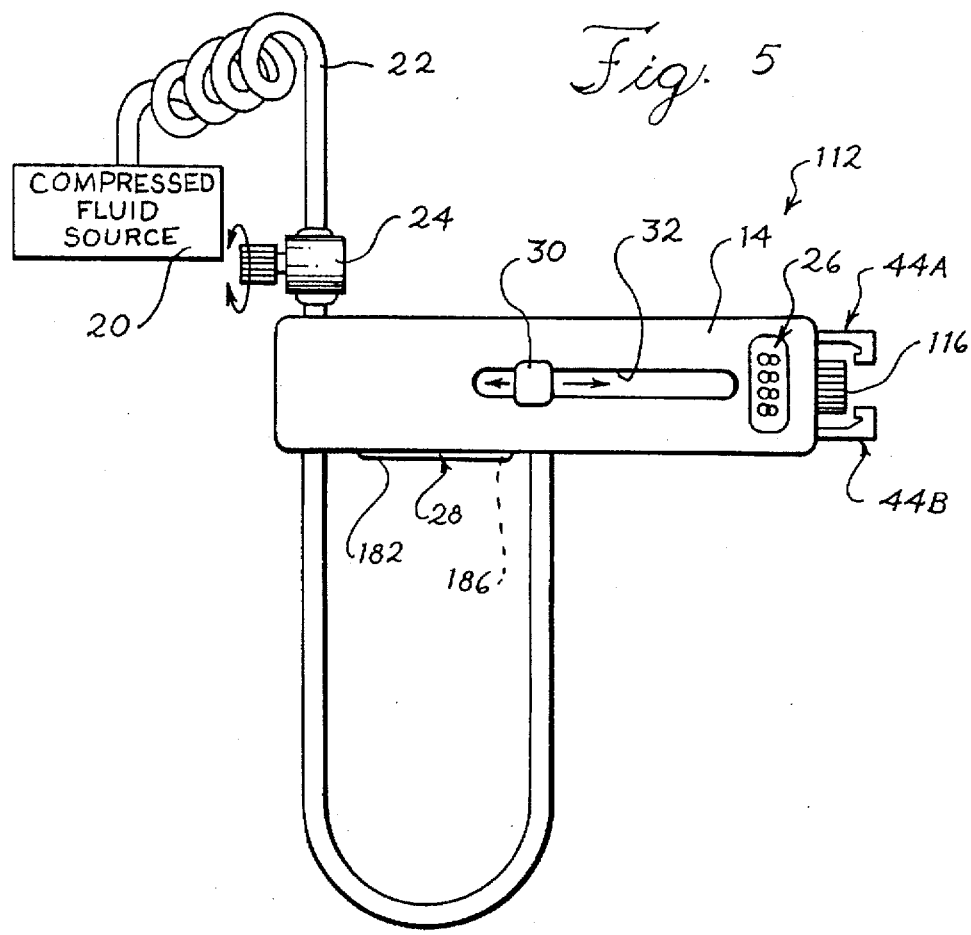
FIG. 5 is a view, similar to that of FIG. 1, of an alternative embodiment of the novel drive assembly releasably joinable with a catheter assembly.

While the invention may be susceptible to embodiment in different forms, there is shown in the drawings, and herein will be described in detail, specific embodiments with the understanding that the present disclosure is to be considered an exemplification of the principles of the invention, and is not intended to limit the invention to that as illustrated and described herein.

Referring initially to FIG. 1, a novel drive assembly 10 is illustrated which is releasably connectable to a novel catheter assembly 12, portions of which are shown in FIGS. 2 through 4, for forming a novelly improved ablation device. The resulting ablation device is intended to solve some, if not all of the above-discussed concerns with the prior art ablation devices. Because the drive assembly 10 is separable from the catheter assembly 12, a medical professional can have greater control over both assemblies 10 and 12, independently and conjunctively, as will be discussed herein.

The drive assembly 10 comprises a body 14 containing, in the illustrated embodiment, an air turbine, not shown, of known construction for imparting a torque on a drive shaft 16, a portion of which is visible projecting from the right hand side of the body 14 as viewed, for driving an ablating burr 18, shown in FIG. 4, which is operatively connected to the drive shaft 16. Other devices for imparting torques to the drive shaft 16 and the ablating burr 18 can be utilized without departing from the scope of the invention. The air turbine is driven by compressed air fed from a compressed air source 20 connected to the turbine by a suitable conduit 22.

The speed of the air turbine, and thus the speed of the drive shaft 16 and the ablating burr 18, is determined by the rate of compressed air flow from the compressed air source 20 to the turbine. In order to control the rate of compressed air flow, a flow regulator 24, such as a needle valve, in the form of a variable orifice valve and the like, is provided on the conduit 22 between the source 20 and the turbine. In the preferred construction, the flow regulator can be varied, thereby controlling the speed of the drive shaft 16 and the ablating burr 18, by hand, and is located proximate to the body 14. In this way, the speed of the ablating burr 18 can be relatively easily controlled as compared to some of the prior art ablation devices. The resulting novel ablation device also uses space more efficiently.

In order to provide a physician with an indication of the rotational speed of the drive shaft 16 and the ablating burr 18, means in the form of a tachometer assembly 26 is provided on the body 14. The tachometer assembly 26 is operatively connected to the drive shaft 16 by suitable means such as by magnets and proximity detectors, for example, and provides the physician with a visual indication of the speed of the ablating burr 18. The tachometer assembly 26 comprises a visual display which may be calibrated to give indications in any desired units, such as revolutions per minute. Because the tachometer assembly 26 and the flow regulator are both located on or near the body 14, the physician may have an easier time in regulating the speed of the ablating burr 18, thereby possibly resulting in a more successful procedure. The tachometer assembly 26 eliminates the need for optical speed detectors and the associated, complex fiber optic assemblies. This allows the drive assembly 10 to make more efficient use of space, as compared to the devices disclosed in the above-referenced Auth patents.

The drive assembly 10 has further means for assisting the physician in ablating a vascular occlusion. A guidewire clamp 28 is attached to the body 14 for releasably holding a portion of a medical guidewire 45, not shown in FIG. 1, used for guiding the catheter assembly 12 to a stenosis or treatment site within the vascular lumen. The clamp 28 can hold the guidewire 45 with respect to the body 14 so that the drive assembly 10 and the guidewire 45 can be moved in unison. The clamp 28 can be applied to and released from the guidewire 45 by appropriate movement of the physician's thumb, palm, or finger so that the clamp 28 holds the guidewire 45 at various locations axially along the guidewire 45. This affords the physician greater flexibility during vascular occlusion material ablation procedures, and also facilitates one-handed operation of the device.

Figure 14:
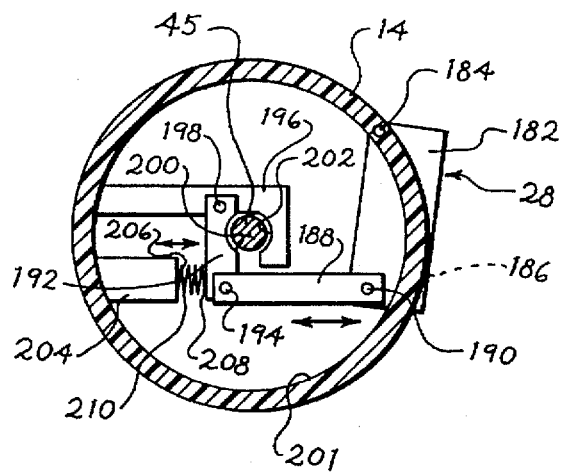
FIG. 14 is a partially sectioned end view of a novel guidewire clamp utilized in a novel drive assembly of the invention.

The particularly novel construction of the guidewire clamp 28 is illustrated in FIG. 14. Specifically, the guidewire clamp 28 includes a plate 182 which is engageable by a physician's thumb, palm or finger. The plate 182 is pivotally connected to the body 14 by a pivot pin 184 such that engagement of the plate 182 causes pivotal movement of the plate 182 about the pivot pin 184. Movement of the plate 182 about the pivot pin 184 allows a portion of the plate 182 to move into and out of the body 14 through an aperture 186 in the body 14.

An end of the plate 182 opposite to the end thereof connected to the body 14 by the pivot pin 184 is pivotally connected to a lever arm 188 within the body 14 by a second pivot pin 190. An end of the lever arm 188 opposite to the end thereof connected to the plate 182 is pivotally connected to a movable contacting arm 192 by a third pivot pin 194. an opposite end of the contacting arms 192 is pivotally connected to a fixed contacting arm 196 by a fourth pivot pin 198 such that the guidewire 45 can be clamped between the contacting arms 192 and 196, as shown in FIG. 14. Specifically, the contacting arms 192 and 196 each include radius ed or semicircular portions 200 and 202, respectively, which conjunctively define a diameter slightly smaller than the outer diameter of a guidewire 45. An end of the contacting arm 196 opposite to the end thereof including the radius ed portion 202 is fixedly attached to an interior surface 201 of the body 14 such that the portions 200 and 202 are relatively movable between a guidewire 45 engaging position and a guidewire 45 releasing position, shown in FIG. 14, in response to movement of the thumb plate 182 for releasably clamping the guidewire 45 against independent axial shifting.

To facilitate shifting of the portions 200 and 202, a bearing member 204 projects from the interior surface 201 of the body 14 adjacent a position at which the contacting arm 196 is attached to the body 14. The bearing member 204 projects a predetermined distance towards the pivoting juncture between the lever arm 188 and the contacting arm 192 to locate a spring contacting surface 206 on the bearing member 204 adjacent a spring contacting surface 208 on the contacting arm 192 proximate to the juncture between the lever arm 188 and the contacting arm 192. A spring 210 is disposed between the contacting surfaces 206 and 208 such that inward movement of the plate 182 shifts the contacting arms 192 and 196 into the guidewire 45 releasing position, shown in FIG. 14, thereby compressing the spring 210. Subsequent relaxation or expansion of the spring 210 causes the contacting arms 192 and 196 to shift into the guidewire 45 engaging position, thereby substantially preventing axial shifting of the guidewire 45. Relaxation of the spring 210 also returns the plate 182 to its original, at rest position. It is to be noted that other constructions of the guidewire clamp 28 are also possible.

A control knob 30 is provided on the body 14 for axially shifting the drive shaft 16 with respect to the body 14. The control knob 30 is attached to the drive shaft 16 by suitable means and is shiftable within an elongate slot 32 in the body 14. In a preferred embodiment, the knob 30 is spring loaded and rachet means, or similar structure, may be located along at least one longitudinal edge of the slot 32 for providing the physician with an audible indication of shifting of the drive shaft 16, and/or to increase tactile feel associated with that shifting as well as providing a locking member for positively maintaining axial positioning of the drive shaft 16 relative to the body 14.

The knob 30 preferably comprises a thumb lock mechanism for shifting the drive shaft 16 responsive to movement of a physician's thumb. This provides for one-handed operation of the device and also provides for smooth movement of the drive shaft 16. Furthermore, the physician can shift the shaft 16 with one simple thumb movement, as compared to the prior an ablation devices where shaft shifting demands two separate, rather complex movements—one to unlock the shaft and one to shift the shaft. Additionally, in the embodiments of the invention, shifting of the knob 30 within the slot 32 induces axial shifting of the drive shaft 16 with respect to the body 14 and the catheter assembly 12, when attached. This means that the drive shaft 16 and the ablating burr 18 can shift axially independent of the assemblies 10 and 12, thereby leading to greater operational flexibility.

The drive assembly 10 also includes flush and cooling means. The drive assembly 10 is provided with a flushing and cooling fluid, such as saline and the like, from an appropriate fluid supply 34 through a suitable conduit 36. The conduit 36 is connected to valving means, not shown, of known construction within the body 14 which direct the fluid into a lumen 38, which is visible projecting from the right hand side, as viewed, of the body 14 in FIG. 1. A fluid-tight luer fitting or connector 40 is provided on the distal end of the lumen 38 for connecting the lumen 38 to the catheter assembly 12, as will be discussed further later. The connector 40 is preferably a female luer connector matable with a complementary male luer connector on the catheter assembly 12. It is to be noted that, in the illustrated embodiment, the drive shaft 16 is located within the lumen 38, and that the lumen 38 and the connector 40 rotate conjointly with the drive shaft 16. Accordingly, the connector 40 also functions as means for connecting the drive shaft 16 of the drive assembly 10 to a drive shaft 42 of the catheter assembly 12. Also, the lumen 38 can supply cooling and flushing fluid to the catheter assembly 12.

The drive shaft 16 extends axially through the lumen 38 so that the fluid therein can cool the drive shaft 16 and the drive shaft 42 during operation.

The drive assembly 10 is releasably connectable to the catheter assembly 12 by complementary means disposed on the drive assembly 10 and the catheter assembly 12. On the drive assembly 10, the means comprises a pair of opposing flexible jaws 44A and 44B extending from a side of the body 14 and flanking the lumen 38. The jaws 44A and 44B are preferably dimensioned such that distal ends thereof terminate short of a proximal end of the connector 40 so that the jaws 44A and 44B can firmly hold the assemblies 10 and 12 together. To facilitate repeatable connection and disconnection of the assemblies 10 and 12, the jaws 44A and 44B are formed from a material having a sufficient degree of elasticity and elastic memory, such as a plastic and the like. The elasticity of the jaws 44A and 44B insures that the jaws 44A and 44B can separate sufficiently to repeatedly accept passage of a proximal portion of the catheter assembly 12, while the elastic memory insures that the jaws 44A and 44B can firmly grasp and retain the catheter assembly 12, even after repeated separations.

The proximal portion of the catheter assembly 12 of FIGS. 2 through 4 comprises a manifold assembly 52, the function of which will become more clear later. The jaws 44A and 44B are configured to engage and to releasably hold an annular flange 46 extending from a proximal end of the manifold assembly 52. Specifically, the jaws 44A and 44B include tabs 48A and 48B, respectively, which are releasably interlockable within an annular notch 50 on the flange 46. The jaws 44A and 44B are relatively offset on the body 14 for accepting the flange 46, thereby insuring a firm connection between the drive assembly 10 and the catheter assembly 12.

The proximal end of the manifold assembly 52 includes structures for facilitating releasable operative joinder of the drive assembly 10 to the catheter assembly 12. Specifically, the manifold assembly 52 includes the drive shaft 42, a fluid tight luer fitting or connector 54, and a fluid sealed bearing 56. Also visible in FIG. 2 is a proximal end of a medical guidewire 45, which can extend axially through the drive shafts 16 and 42 and can be proximally releasably held in place by the clamp 28, as discussed above. The drive shaft 42 extends through the entire axial length of the catheter assembly 12, and its proximal end passes through to the connector 54, while its distal end is connected to the ablating burr 18.

It is to be noted that the coiled construction of the drive shaft 42 shown in FIGS. 3, 4 and 7 is exaggerated for clarity, viz. the drive shaft 42 comprises coils tightly wound such that there are no gaps between adjacent coils. The drive shaft 42 preferably includes a guidewire lumen 43 for accepting the guidewire 45 in common fashion in much the same way as the drive shaft 16 accepts the guidewire 45. The drive shaft 42 is preferably constructed such that the drive shaft 42 does not appreciably radially contract upon the guidewire 45 disposed within the guidewire lumen 43 during operation of the ablation device 10, thereby reducing friction between the drive shaft 42 and the guidewire 45. In addition, the guidewire lumen 43 may be coated with a lubricous substance, such as TEFLON® and the like, for reducing friction between the outer diameter surface of the guidewire 45 and the inner diameter surface of the drive shaft 42. By reducing friction between the drive shaft 42 and the guidewire 45 disposed within the guidewire lumen 43, conjoint rotation of the drive shaft 42 and the guidewire 45 is substantially limited. This is an improvement over some of the ablation devices of the prior art having a guidewire that rotates conjointly with a drive shaft during an ablation procedure.

The connector 40 is releasably connectable to the connector 54 so that torque on the drive shaft 16 can be effectively transmitted to the drive shaft 42, and thus to the ablating burr 18. The connector 54 is releasably joinable with the connector 40 to also provide a fluid tight connection between the drive assembly 10 and the catheter assembly 12 so that cooling and flushing fluid can flow from the drive assembly 10 into and through the catheter assembly 12. In the illustrated embodiment, the connector 54 is a male luer fitting releasably insertable into the female connector 40. In addition, to insure a secure fit between the connectors 40 and 54, the connector 40 has internal threads 58 engageable with external threads 60 on the connector 54. The threads 58 and 60 are oriented such that conjoint rotation of the connectors 40 and 54 will not adversely effect the connection therebetween.

A distal end of the connector 54 is fixed to the bearing 56. The bearing 56 is dimensioned for insertion into a fluid lumen 62 in the manifold assembly 52 so that fluid can flow through the connector 54 and the bearing 56 into the lumen 62. The bearing 56 is axially shiftable within the lumen 62 to facilitate joinder and separation of the assemblies 10 and 12, and provides a proximal, fluid tight seal of the fluid lumen 62. The bearing 56 also rotates conjointly with the connectors 40 and 54 in response to rotation of the drive shaft 16. In this manner, fluid in the lumen 62 can flow into the remainder of the catheter assembly 12 during operation of the device. It is to be noted that the drive shaft 42 extends axially through the bearing 56 and the lumen 62, and through the remainder of the catheter assembly 12 to the ablating burr 18. Thus, the manifold assembly 52 should be able to supply cooling fluid along the axial length of the drive shaft 42.

In the embodiment illustrated in FIG. 2, the manifold assembly 52 comprises a main body 64 and a cap 66 joined to the main body 64 by appropriate means 68, such as an adhesive and the like. The means 68 also attaches a catheter tube 70 to the cap 66 for insertion into a patient's vascular system. Therefore, the drive assembly 10 and the manifold assembly 52 are intended to remain outside of the patient's body during vascular occlusion material ablation. The cap 66 includes a fluid lumen 72 for accepting fluid and the drive shaft 42, and another lumen 74, connected to a luer fitting or port 76, accessible from the exterior of the manifold assembly 52, on the cap 66, for supplying the catheter tube 70 with a drug therapy to be delivered to the treatment site, or with positive or negative pressure for a dilating device, such as a balloon, or for aspiration of the treatment site, respectively. It is to be noted that, if the treatment site is aspirated, it is desirable to also irrigate the treatment site by a corresponding amount to maintain the condition of the vasculature. This conjunctive aspiration and irrigation can be achieved, for example, with utilization of the structure illustrated in FIG. 10, as will be discussed further later.

Figure 6:
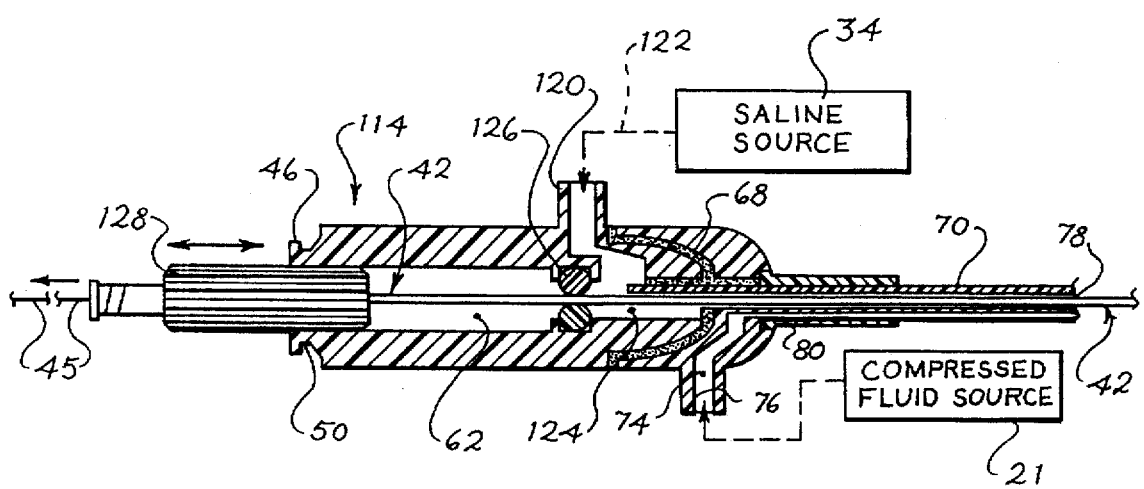
FIG. 6 is a partially sectioned side elevational view of an alternative embodiment of a manifold assembly comprising a proximal portion of a catheter assembly releasably joinable to the drive assembly of FIG. 5.

An alternative embodiment of the releasably attachable drive assembly and catheter assembly is illustrated in FIGS. 5 and 6. A drive assembly 112 is shown in FIG. 5 and a complementary releasably attachable manifold assembly 114 is shown in FIG. 6. The drive assembly 112 and the manifold assembly 114 are substantially similar to the drive assembly 10 and the manifold assembly 52, respectively, except for the differences to be noted herein, hence the like reference numerals for similar structures. It is also to be noted that the relevant portions of the catheter assembly 12 shown in FIGS. 3 and 4 can be used with both manifold assemblies 52 and 114.

The drive assembly 112 differs from the drive assembly 10 in that the drive assembly 112 is not directly connected to a cooling fluid supply 34, and therefore, lacks the fluid lumen 38. Cooling fluid is supplied directly to the manifold assembly 114. The drive shaft 16 of the assembly 112 is connected to a keyed drive shaft connector 116, which is the only operative portion of the drive shaft 16 that extends outside the body 14. The drive shaft connector 116 forms a positive link between the drive shaft 16 of the drive assembly 112 and the drive shaft 42 of the catheter assembly 12 so that torque on the drive shaft 16 can be transmitted to the drive shaft 42.

The construction of the associated manifold assembly 114 is shown in FIG. 6. The assembly 114 comprises a main body 118 joined to a cap 66 by adhesive means 68, however, while the cap 66 on the assembly 114 is substantially similar to the cap 66 on the assembly 52, the main body 118 of the assembly 114 is different from the main body 64 of the assembly 52. Specifically, because the drive assembly 112 lacks a connection to a cooling fluid supply 34, the main body 118 includes a cooling fluid luer fitting or port 120 connectable to a cooling fluid supply 34 by a suitable conduit 122. The fluid port 120 communicates with a fluid lumen 124 within the main body 118 for directing cooling fluid from the port 120 to the drive lumen 78 in the catheter tube 70.

Because the drive assembly 112 lacks the connector 40, it is desirable to prevent cooling fluid flow towards the drive assembly 112. In order to prevent this fluid flow, a fluid-tight seal bearing 126 is provided at an end of the fluid lumen 124 opposite to the end thereof connected to the drive lumen 78 of the catheter tube 70. The drive shaft 42 extends through the bearing 126 for connection to the keyed connector 116 on the drive assembly 112. The drive shaft 42 extends through the bearing 126 and the fluid lumen 62 where it is fixedly mounted to a rotatable bearing 128, substantially similar to the bearing 56, which allows fluid to flow into and out of the fluid lumen 62 in the proximal portion of the manifold assembly 114.

A proximal end of the bearing 128 includes suitable means, not shown, which mate with the keyed configuration of the drive shaft connector 116 on the drive assembly 112 for insuring joinder of the drive shaft 16 to the drive shaft 42. To facilitate joinder of the drive shafts 16 and 42, the bearing 128 is axially shiftable within the fluid lumen 62 in the main body 118. The connector 116 and the bearing 128 also allow for passage of the guidewire 45 therethrough. As noted hereinabove, each manifold assembly 52 and 114 can utilize the same catheter tube 70.

The construction of the catheter tube 70 is shown more clearly in FIG. 3. The fluid lumen 72 communicates with a corresponding lumen 78 in the catheter tube 70 for accepting cooling fluid and the drive shaft 42, and the lumen 74 communicates with another lumen 80 in the catheter tube 70 radially offset from the lumen 78. In the embodiment shown in FIG. 2, the means 68 can form a seal on the proximate ends of the lumens 78 and 80, which, in conjunction with the particular luminal construction of the catheter tube 70 insures complete functional independence of the lumens 78 and 80. Thus, if the lumen 80 were used for aspiration, there would be no chance that aspirated particles or stenosis debris could interfere with operation of the drive shaft 42 within the lumen 78, as opposed to the prior art ablation devices discussed earlier.

Another novel structure, viz. a drive shaft sheath 79, within the catheter tube 70 is shown in FIGS. 3 and 4. The drive shaft sheath 79 overlies an outer diameter surface of the drive shaft 42 and has an axial length substantially equal to the axial length of the drive shaft 42. Specifically, the drive shaft sheath 79 extends from a position adjacent a distal end of the bearing 56 to a position between the distal end of the catheter tube 70 and a proximal end of the ablating burr 18. The drive shaft sheath 79 substantially seals the drive shaft 42, thereby substantially preventing escape of fluids disposed within the drive shaft 42, and notably the guidewire lumen 43, from the drive shaft 42 and the drive shaft sheath 79. In this manner, irrigation or cooling fluid supplied by the fluid source 34 can flow into the guidewire lumen 43 within the drive shaft 42 and axially flow within the space between the drive shaft 42 and the guidewire 45. The drive shaft sheath 79 positively retains the fluid between the guidewire 45 and the drive shaft 42 for providing effective cooling of the drive shaft 42 during operation of the ablation device 10.

This is a significant improvement over some of the ablation devices of the prior art wherein fluid introduced into a lumen between a guidewire and a coiled drive shaft may flow through coils comprising the drive shaft because a gap between an outer diameter surface of the drive shaft and a drive shaft lumen within a catheter tube is larger than a corresponding gap between an outer diameter surface of a guidewire and a guidewire lumen within a drive shaft. The larger gap presents a fluid flow path having less resistance to fluid flow therethrough, thereby causing significant fluid loss from the guidewire lumen, which may lead to inefficient cooling of the drive shaft during operation.

The particular luminal construction of the catheter tube 70 may be more clearly understood with reference to FIG. 9, which shows a cross section of the catheter tube 70. FIG. 9 shows a catheter tube 70 containing a plurality of smaller diameter lumens and elements, viz. the drive shaft 42 having a guidewire lumen 43 accepting the guidewire 45, and the fluid or drive shaft lumen 72, which are all substantially concentrically disposed within the tube 70. However, as noted hereinabove, the lumen 80 is offset radially from the lumen 72 and is not disposed concentrically with the lumen 72, thereby allowing completely independent operation of the lumens 72 and 80. Specifically, the lumen 80 has an axis of elongation radially offset within the tube 70 such that that axis is parallelly offset from an axis of elongation of the lumen 72.

In addition, it is to be noted that, while the lumen 72 has a substantially circular latitudinal cross section, the lumen 80 has a substantially elliptical latitudinal cross section. The elliptical cross section of the lumen 80 allows the lumen 80 to be included within the catheter tube 70 without having to appreciably expand the outer diameter of the tube 70. Furthermore, as shown in FIG. 10, the elliptical cross section of the lumen 80 allows for additional, functionally independent lumens, such as the lumen 86, to be disposed within the tube 70 without appreciably increasing the outer diameter of the catheter tube 70. The provision of these added lumens 80 and 86 gives the physician greater flexibility during a vascular occlusion material ablation procedure. For example, the lumens 80 or 86 can be used to carry a positive or negative pressure fluid from a compressed fluid source 21 to the dilating member 82 for inflation thereof. Alternatively, the lumens 80 or 86 can be used to transport drug therapy or other infusion to a treatment site, or to carry a negative pressure to the treatment site for the aspiration thereof. In addition, from a manufacturing standpoint, the luminal constructions illustrated in FIGS. 9 and 10 can be manufactured relatively easily, by extrusion methods and the like, as compared to the prior an ablation device catheter assemblies which may require some form of radial support or interconnection among the concentric lumens. The distal end of the catheter tube 70 is shown in FIG. 4. The catheter tube 70 illustrated includes a dilating member 82 in the form of a balloon deformable or inflatable responsive to pressures in the lumen 80. In order to direct positive pressure into the dilating member 82, a plug 84 is installed at a distal end of the lumen 80 such that pressures applied to the lumen 80 from the fluid source 21 are contained therein. The plug 84 may comprise a suitable amount of adhesive, an elastomeric member, or similar structure and material. The lumen 80 has an aperture 85 proximate to the plug 84 and communicating with the interior of the member 82. The aperture 85 allows pressures within the lumen 80 to flow into the interior of the member 82, thereby inflating or deflating it. While the lumen 80 is illustrated in FIG. 4 as terminating short of the lumen 78, it is to be noted that the lumens 78 and 80 can terminate at the same axial location.

The member 82 is disposed around the entire circumference of the catheter tube 70 adjacent the aperture 85, is of known construction, and is intended to allow the medical professional to perform angioplasty or similar procedure in conjunction with vascular occlusion material by ablation. In addition, by dilating the member 82 sufficiently to engage the interior surface of a patient's vascular lumen with an outer surface of the member 82, the physician can use the contact between the vascular lumen and the dilating member 82 as a fulcrum for applying forces to portions of the catheter tube 70 located distally of the dilating member 82. Inflation of the dilating member 82 can center the ablating burr 18 relative to a vessel in which the ablation device 10 is inserted and which is located proximally of an occlusion to be ablated. The dilating member 82 may also prevent the drive shaft 42 and the catheter tube 70 from leaping forward in the patient's vasculature. This can provide the physician with increased navigability of the catheter tube 70, and with increased options during vascular occlusion material ablation procedures.

As FIG. 4 shows, an annulus or ring 88 is disposed proximate the distal end of the catheter tube 70, and specifically around the circumference of the distal end of the exterior surface of the lumen 78. If the lumens 78 and 80 co-terminate, then the ring 88 circumscribes both lumens 78 and 80. The ring 88 is formed from a radiopaque material, thereby rendering the distal end of the catheter tube 70 visible to a physician monitoring progress of the catheter tube 70 within the patient's vascular system by radiography or similar imaging technique. This is a substantial improvement over the ablation catheters of the prior art wherein only a distal end of the associated guidewire is radiopaque.

The distal end of the drive shaft 42 extends axially out of the lumen 78 and beyond the distal end of the catheter tube 70 where the drive shaft 42 is connected to the ablating burr 18 by suitable means. The construction of the ablating burr 18 will be discussed in further detail later. The ablating burr 18 has a central bore or lumen, not shown, for allowing the guidewire 45 to pass therethrough. The guidewire 45 extends through the ablating burr 18 and terminates at a coil or spring 90. The size of the spring in FIG. 4 is exaggerated for rarity, and actually, the spring 90 defines an outer diameter substantially equal to the outer diameter of the guidewire 45. The spring 90 is usually comprised of a radiopaque material. It is envisioned that many different guidewire constructions can be utilized with the embodiments of the present invention without departing from the intended scope thereof, thereby providing greater guidewire compatibility.

The specific ablating burr 18 shown in FIG. 4 is but one embodiment thereof, and different constructions can be utilized to achieve different ablation results. The ablating burr 18 is a substantially ellipsoidal body having an abrasive coating 92 disposed over a distal half thereof defined by a latitudinal midline of the burr 18. This particular disposition of abrasive 92 allows the ablating burr 18 to ablate along a three hundred and sixty degree arc within the vascular lumen responsive to rotation of the drive shaft 42, substantially similar to the ablation or ablating performed by the prior art ablation devices. This type of ablation may be desirable in certain situations where the deposits forming the stenosis are located substantially along a three hundred and sixty degree arc along the interior surface of the vascular lumen. However, this may not always be the case.

If the stenosis deposits are eccentric, as may often be the case, the physician may wish to subject a subset of the three hundred and sixty degree arc on the interior surface of the vascular lumen to the ablation effects of the ablation device. A novel construction for ablating or ablating a subset of a three hundred and sixty degree arc within a vascular lumen is illustrated in FIGS. 7 and 11. The construction of FIG. 7 employs an ablating shield 96 extending from a distal end of the catheter tube 70. Specifically, the ablating shield 96 extends axially from the distal end of the catheter tube 70 a distance sufficient to locate a distal end 98 of the ablating shield 96 forward or distally of a latitudinal midline of the ablating burr 18. The ablating shield 96 also extends substantially radially from the distal end of the catheter tube 70 a distance sufficient to offset the shield 96 radially from the ablating burr 18 such that the ablating shield 96 does not interfere with rotation of the burr 18. To further insure that the ablating shield 96 does not interfere with rotation of the ablating burr 18, portions of the ablating shield 96 adjacent the ablating burr 18 may be coated with a lubricious substance, such as TEFLON® and the like, or may be subjected to a hard coating process such that those portions are not ablated by the abrasive 92 on the ablating burr 18. Alternatively, the abrasive 92 can be located on the ablating burr 18 such that portions of the ablating burr 18 which can contact an ablating shield 96 do not include abrasive 92.

However, the shield 96 can be placed between a periphery of the ablating burr 18 and a portion of an interior surface of the vascular lumen, thereby shielding that portion from the ablating effects of the ablating burr 18. By appropriate placement of the ablating shield 96 with respect to the vascular lumen and the ablating burr 18, the relevant portion of the vascular lumen will not be exposed to the ablating burr 18. Furthermore, if it is desirable, the ablating burr 18 can be axially shifted, as described above, with respect to the catheter tube 70 and the ablating shield 96 in order to locate the entirety of the abrasive coating 92 forward or distally of the distal end 98 of the ablating shield 96, in order to subject a three hundred and sixty degree arc on the interior surface of the vascular lumen to the ablating effects of the burr 18.

The structure of the embodiment of FIG. 11 differs somewhat from the structure illustrated in FIG. 7. The embodiment of FIG. 11 comprises an ablating shield 104 which is essentially an extension of a portion of the catheter tube 103. Specifically, the ablating shield 104 comprises a trough-like extension of a less than three hundred and sixty degree arcuate portion of the catheter tube 103 for shielding a corresponding portion of the interior surface of the vascular lumen from abrasion or ablation. The angular measure of the arc defined by the ablation shield 104 may be pre-determined for different applications. The embodiment of FIG. 11 also utilizes an ablating burr 105 which differs from the ablating burr 18 in that the burr 105 does not have an axial bore therethrough to accommodate the guidewire 45.

To account for the lack of the guidewire lumen 43, a separate guidewire lumen 106 is provided on the outer surface of the catheter tube 70 and the ablation shield 104. The lumen 106 extends from a location adjacent the distal side of the ring 88 to the distal edge of the ablation shield 104. Because the guidewire lumen 106 does not extend along the entire axial length of the catheter tube 70, the effective length of the guidewire 45 is reduced, viz. the length of the guidewire 45 within the guidewire lumen 106 at any given moment is substantially less than the length of the guidewire 45 within the guidewire lumen 43. Thus, the catheter tube 70 of the embodiment of FIG. 11 is relatively more maneuverable with respect to the guidewire 45, and allows for quicker and easier exchange, as compared to the catheter tube 70 of the embodiments of FIGS. 1 through 10.

In the FIG. 11 embodiment as well, the ablating burr 105 is axially shiftable with respect to the catheter tube 70 and the ablation shield 104. However, because the guidewire 45 extends beyond the distal end of the ablating shield 104, the guidewire 45 may interfere with the operation of the ablating burr 105 if the ablating burr 105 were shifted beyond the distal end of the ablating shield 104. Similar difficulties may be encountered with other, similarly constructed guidewire lumens employed by some prior art ablation devices.

To avoid these difficulties, the invention provides the embodiment illustrated in FIG. 12. This embodiment comprises a catheter tube 108 having a drive shaft lumen 78 and a separate guidewire lumen 110 located along a circumference of the lumen 78 such that the lumens 78 and 110 are not concentric. The guidewire lumen 110 extends axially through a thickness of the catheter tube 108. This allows the ablating burr 105 to be attached to the distal end of the drive shaft 42 and also allows the ablating burr 105 to be axially shifted and operated forward or distally of the distal end of the catheter tube 108 without interference with the guidewire 45, as distinguished from the embodiment of FIG. 11.

The guidewire 45 can be axially shifted within the guidewire lumen 110 among positions proximally and distally of the ablating burr 105. In operation, the guidewire 45 can be shifted into an extended position with the distal end and spring 90 of the guidewire 45 being in front of the distal end of the ablating burr 105 for guiding the ablating burr 105 to the intravascular treatment site. Once the treatment site has been reached, the guidewire 45 can be shifted into a retracted position, illustrated in FIG. 12, where the distal end and spring 90 of the guidewire 45 are located behind a proximal end of the ablating burr 105. Thus, the ablating burr 105 may rotate and ablate the stenosis substantially free from interference with the guidewire 45. This can provide a treating physician with greater operative flexibility during vascular occlusion material ablation procedures.

As discussed earlier, it may be desirable to change ablating burrs during a vascular occlusion material ablation procedure to account for configuration variations and morphology of the deposits forming a particular stenosis. This embodiment of the invention provides novel means for changing ablating burrs without having to also change the entire catheter assembly. One such means is the catheter assembly 158 illustrated in FIG. 8. This novelly constructed catheter assembly 158 comprises an elongate catheter tube 160 intravascularly insertable into a patient's vasculature. The tube 160 may have a plurality of lumens therein, and may have a latitudinal cross section similar to those shown in FIGS. 9 and 10.

The catheter tube 160 has at least a drive shaft lumen 162 through which is disposed a drive shaft 164 for applying force to a novel ablating burr 166. The drive shaft 164 itself has a unique construction. Specifically, the distal end of the drive shaft 164 includes a portion of the means for changing ablating burrs in the form of a socket or connection member 168, and also has a guidewire lumen 167 for accepting a guidewire 45. The connection member 168 is fixedly attached to the distal end of the drive shaft 164 such that the member 168 extends distally beyond a radiopaque ring 88 disposed on a distal portion of the tube 160. The connection between the drive shaft 164 and the connection member 168 allows for efficient torque transfer from the drive shaft 164 to the member 168 so that the shaft 164 and the member 168 rotate conjointly. The illustrated embodiment of the connection member 168 has threads 170 thereon for engagement with corresponding threads on the ablating burr 166. Other attachment means may also be used. The ablating burr 166 comprises a substantially ellipsoidal body 172 having an abrasive coating disposed on at least one half thereof. The body 172 has a guidewire lumen 174 extending axially therethrough for allowing passage of the guidewire 45, substantially similar to that shown in FIG. 4. A proximal end of the body 172 is fixedly attached to another portion of the means for changing ablating burrs in the form of a projection 176.

The projection 176 is substantially cylindrical having an enlarged, disk-shaped flange portion 178 for facilitating torque transfer to the ablating burr 166 and also to insure firm attachment of the body 172 to the projection 176. The projection 176 also has threads 180 thereon which are releasably threadibly engageable with the threads 170 on the member 168 for forming a firm connection between the drive shaft 164 and the ablating burr 166. The threads 170 and 180 are configured such that rotation of the drive shaft 164 and/or the ablating burr 166 will not cause the threads 170 and 180 to become disconnected. A guidewire lumen, not shown in the Figures, also extends through the projection 176 so that the guidewire 45 can extend through the lumen 167, through the member 168 and the projection 176, and through the ablating burr 166 for intravascularly navigating the catheter assembly 158.

The ablating burr 166 may have different configurations and dimensions, and also the configuration and composition of the abrasive on the ablating burr 166 may be different. The connection between the threads 170 and 180 insures efficient torque transfer between the drive shaft 164 and the ablating burr 166 and allows a physician to quickly change ablating burrs 166 without having to replace the entire catheter assembly. In the preferred embodiment, the member 168 has internal female threads 170 and the projection 176 has external male threads 180, and the projection 176 is insertable into the member 168 for engaging the threads 170 with the threads 180.

Illustrating the construction of this embodiment further by example, the physician chooses an appropriate ablating burr 166 dependent upon the particular stenosis to be ablated. The projection 176 on the ablating burr 166 is inserted into the member 168 such that the threads 180 engage the threads 170. The burr 166 is rotated with respect to the member 168, thereby threadibly attaching the burr 166 to the member 168 and the drive shaft 164. The physician then inserts the burr 166 and the catheter tube 160 into the patient and energizes the ablating burr 166 to ablate the stenosis or occlusion.

If it becomes desirable to change the ablating burr 166 because of wear on the burr 166, configuration of the stenosis, or the like, the physician can withdraw the catheter tube 160 from the patient's vascular system. Upon withdraw of the distal end thereof from the patient, the physician can remove the attached ablating burr 166 by application of suitable forces, thereby disengaging the threads 170 from the threads 180. With the first ablating burr 166 being thusly removed, another ablating burr 166, possibly having different ablating characteristics, may be attached to the catheter tube 160 by performing the same steps described hereinabove in reverse order.

Figure 13:
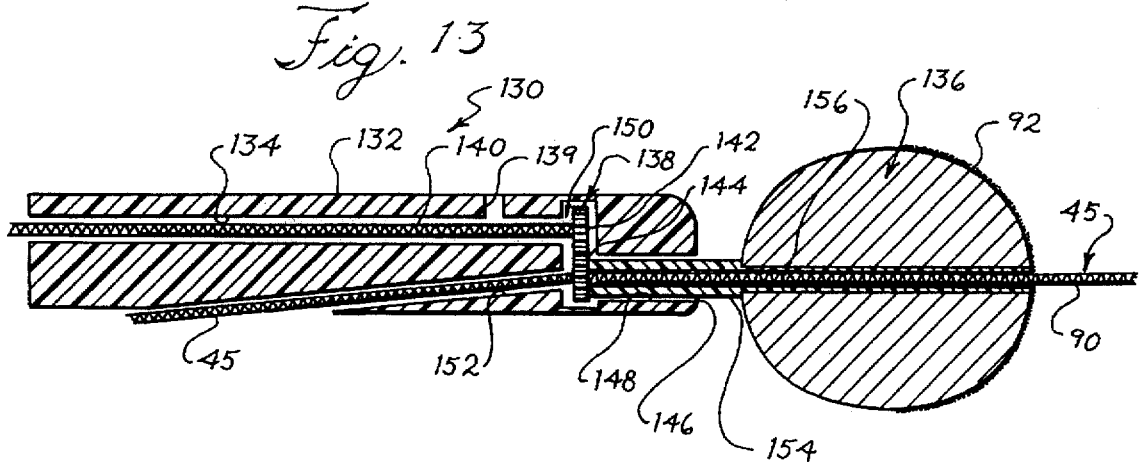
FIG. 13 is a partially sectioned side elevational view of a further embodiment of the distal end of a novel catheter assembly of the present invention.

Another embodiment of the invention is the catheter assembly 130 illustrated in FIG. 13, only the distal portion of which is shown, which allows for increased maneuverability of the catheter assembly 130 with respect to a guidewire 45, and for quicker and easier exchange as compared to the catheter tube 70 of the embodiments of FIGS. 1 through 10. It is to be noted that the proximal portion of the catheter assembly 130 may be of any suitable construction sufficient to support the illustrated construction of the distal portion. The distal portion of the catheter assembly 130 comprises a catheter tube 132 having a drive shaft lumen 134 extending axially therethrough, however, the drive shaft lumen 134 is preferably not located centrally along the axial length of the catheter tube 132. This provides clearance for drive means 138 which rotatably drives an ablating burr 136. The drive shaft lumen 134 also has a cooling fluid outlet port 139 proximate a distal end thereof for allowing cooling fluid within the lumen 134 to flow therethrough. A drive shaft 140 extends axially through the drive shaft lumen 134, and has a portion of the means 138, specifically a toothed drive gear 142, attached to the distal end of the shaft 140. The drive gear 142 meshes with a complementary drive gear 144 operatively connected to the ablating burr 136 for rotating the ablating burr 136 in response to rotation of the drive shaft 140.

The ablating burr 136 includes a shaft 146 projecting substantially centrally axially from the burr 136. The shaft 146 extends through a suitable lumen 148 in the distal end of the catheter tube 132. An end of the shaft 146 opposite to the end thereof connected to the ablating burr 136 is connected to the drive gear 144, which is journally located inside the catheter tube 132. The catheter tube 132 has a drive lumen 150 extending substantially perpendicular between the drive shaft lumen 134 and the lumen 148. The drive lumen 150 is dimensioned for accepting the drive means 138, and allows the drive gear 142 to engage the gear 144, thereby accomplishing effective torque transfer from the drive shaft 140 to the ablating burr 136.

The catheter tube 132 also has a guidewire lumen 152 which extends through the distal portion of the tube 132 substantially tangentially to the axis of elongation of the tube 132. The guidewire 45 enters the catheter tube 132 at an angle sloping towards the axis of elongation thereof, but, because the guidewire lumen 152 terminates at the drive lumen 150, the guidewire 45 can be curved such that the guidewire 45 extends substantially parallel to the axis of elongation distally of the drive lumen 150. The shaft 146 has a through bore 154 which communicates with a corresponding through bore 156 in the ablating burr 136. Thus, the guidewire 45 can pass through the guidewire lumen 152, through the drive lumen 150, the bore 154 and the bore 156, and extend beyond the distal end of the ablating burr 136, as shown in FIG. 13, for guiding the catheter tube 132 and the ablating burr 136 to the intravascular treatment site. Because the effective length of the guidewire 45 disposed within the catheter tube 132 is reduced, as compared to the embodiments of the invention illustrated in FIGS. 1 through 10, the catheter tube 132 is relatively more maneuverable with respect to the guidewire 45, and provides for quicker and easier exchanges.

The above-discussed embodiments of the invention provide significant improvements over the ablation devices of the prior art, and specifically over the ablation devices disclosed in the above-cited Auth patents. Specifically, by providing an ablation device comprising releasably joinable drive and catheter assemblies, the catheter tube is more delicately and precisely maneuverable or navigable within a patient's vascular lumen. The physician's tactile feel of the progression of the catheter tube through a vascular lumen is not reduced by connection between the drive assembly and the catheter assembly. The separable drive and catheter assemblies also provide for easier, quicker ablating burr changes, making it easier for a treating physician to adapt the size of the ablating burr to correspond to the geometry, hardness, and other relevant characteristics of the occlusion to be ablated. This may also possibly allow for a reduction of the costs of a vascular occlusion material ablation procedure because multiple equipment is not required.

The particularly novel construction of the drive assemblies 10 and 112 also allows for substantially one-handed operation thereof, because cumbersome effects of assembly attachments are reduced, thereby further increasing ease of operation for a physician. Additionally, because the drive assemblies are releasably attachable to a plurality of catheter assemblies, the embodiments of the invention provide greater compatibility with other catheter assemblies, as compared to the prior an ablation devices.

The embodiments of the invention also provide a number of ways for relatively inexpensively changing the ablating characteristics of an ablating burr, or for changing the ablating burr itself. The ablating burrs of the different embodiments can ablate a specific portion of the interior surface of a vascular lumen. Because the drive assembly and the catheter assembly are releasably connectable, a different catheter having a different ablating burr or ablating shield may be easily attached to the drive assembly. Also, ablating burrs having threads for threadibly attachment to a drive shaft may also be provided, thereby allowing change of ablating burrs by simply unscrewing one burr from the drive shaft and screwing on another ablating burr. Because of this adaptability, the various embodiments of the invention provide ablation devices that may have greater indications for use than some prior art ablation devices.

The embodiments of the invention also provide novel means for ablating along a particular portion of an interior surface of a vascular lumen. By using an ablating shield, a physician can insure that only diseased tissue is ablated and that healthy tissue is protected. This may be particularly desirable for ablating eccentric stenosis deposits from a lumen. Also, the embodiments of the invention provide a way for eliminating interference with the operation of the ablating burr by the guidewire 45.

Further improvements are presented by the novel debris removal means and a dilating member 82. The debris removal means of the above discussed embodiments prevents debris from interfering with operation of the ablating burr, while being relatively easy to manufacture. The debris removal means also allows for catheter lumens to be constructed for and dedicated to a particular purpose. The teachings of the construction of the debris removal means may also be employed in delivering drug treatments or other infusions to a treatment site, or pressure from the fluid source 21 to a dilating member 82. The dilating member 82 allows a physician to perform both occlusion material ablation and occlusion material molding, or angioplasty, or similar procedures, with the same catheter assembly, thereby possibly further reducing materials necessary for the procedures. The dilating member 82 can also be used as a fulcrum, thereby providing a physician with increased navigability of the catheter assembly within a vascular lumen.

The various embodiments of the present invention also provide greater compatibility with a plurality of different guidewires 45, especially guidewires 45 having a diameter measuring 0.014 inches and 0.018 inches, which tend to be quite popular. The embodiments can be used with guidewires 45 having outer diameters measuring, for example, substantially within the range of 0.01 to 0.02 inches. Thus, a treating physician is not limited to a particular guidewire 45 by the construction of the ablation device, thereby allowing a physician to use the guidewire 45 of preference for a particular application, or the guidewire 45 with which the physician has particular skill. This renders the ablation devices of the invention more compatible with preexisting PTCA equipment, as opposed to the prior an ablation devices which may have limited compatibility.

The greater guidewire 45 compatibility of the embodiments of the invention also increases the tractability of the device over the guidewire 45, and may increase the physician's tactile feel relating to profession of the device over the guidewire 45. This greater compatibility allows a treating physician to use his guidewire of choice, which may be important to the physician if, for example, he has developed substantial skill with a particular guidewire. These things can facilitate intravascular navigation of the device over the guidewire 45, and may eliminate or reduce the need to rotate the drive shaft with respect to the device in order to maintain good tractability and pushability.

The novelly improved ablation devices of the invention give the treating physician greater visual indicia of operation of the device. The ring 88, in addition to the spring 90 often found at the distal end of the guidewire 45, renders the distal end of the associated catheter assembly radioscopically visible to the treating physician, thereby allowing the physician to positively locate the device with respect to a stenosis or other vascular obstruction. The embodiments of the invention also provide means to monitor and adjust the speed of an ablating burr within the vascular lumen. This means allows the physician to positively set the speed of movement of the ablating burr. Also, because this means is located on the drive assembly itself, one-handed operation is still possible, and this novel device utilizes space more effectively than the prior art ablation devices.

The embodiments of the invention provide novel improvements in an ablation device which can significantly facilitate vascular occlusion material ablation procedures. It is to be clearly understood that while a plurality of different embodiments of the invention are presented separately herein, these embodiments may be included in any desired combination on an ablation or other intravascular treatment device. While preferred embodiments of the present invention are shown and described, it is envisioned that those skilled in the art may devise various modifications of the present invention without departing from the spirit and scope of the appended claims.

We claim:

1. A drive assembly of an ablation device connectable to a catheter assembly including a rotatable drive shaft, the drive assembly comprising:

a housing; and a connector including a first coupling rotatably connected to the housing about an axis of rotation, the first coupling including means for releasably connecting the drive shaft to the housing for rotating the drive shaft relative to the housing, and the first coupling including a fluid tight seal to allow fluid to flow between the housing and the catheter assembly; and the connector including a second coupling fixedly connected to the housing and including means for releasably connecting a portion of the catheter assembly to the housing, the second coupling retaining the portion of the catheter assembly from rotation relative to the housing while the first coupling rotates with the drive shaft.

2. A connector in accordance with claim 1, wherein the first coupling is slidably connected to the housing to allow the position of the first coupling to be shifted along the axis of rotation.

3. A connector in accordance with claim 1, wherein the first coupling includes an internally threaded connector capable of threadably connecting the drive shaft to the housing.

4. A connector in accordance with claim 1, wherein the second coupling includes two generally opposing flexible jaws extending from the housing.

5. A connector in accordance with claim 4, wherein each jaw includes a tab engagable with the catheter assembly to connect the portion of the catheter assembly to the housing.

6. A connector in accordance with claim 5, wherein the jaws are formed at least in part from a resilient plastic.

* * * * *